United States Patent
Cuello et al.

(10) Patent No.: US 11,274,290 B2
(45) Date of Patent: Mar. 15, 2022

(54) COMBINED ELICITATION FOR ENHANCEMENT OF CELL GROWTH AND PRODUCTION OF SECONDARY METABOLITES IN MICROALGAE CULTURES

(71) Applicant: ARIZONA BOARD OF REGENTS ON BEHALF OF THE UNIVERSITY OF ARIZONA, Tucson, AZ (US)

(72) Inventors: Joel L. Cuello, Tucson, AZ (US); Chen-Han Shih, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 127 days.

(21) Appl. No.: 16/686,707

(22) Filed: Nov. 18, 2019

(65) Prior Publication Data
US 2020/0157524 A1    May 21, 2020

Related U.S. Application Data

(60) Provisional application No. 62/768,509, filed on Nov. 16, 2018.

(51) Int. Cl.
| | | |
|---|---|---|
| *C12N 13/00* | (2006.01) | |
| *C12N 1/12* | (2006.01) | |
| *C12P 23/00* | (2006.01) | |
| *A01G 33/00* | (2006.01) | |
| *C12M 1/00* | (2006.01) | |

(52) U.S. Cl.
CPC .............. *C12N 13/00* (2013.01); *A01G 33/00* (2013.01); *C12M 21/02* (2013.01); *C12N 1/12* (2013.01); *C12P 23/00* (2013.01)

(58) Field of Classification Search
CPC .... C12N 15/1037; C12N 15/00; C12N 15/70; C12N 15/74; C12N 13/00; C12N 1/12; C12N 15/87; C12N 1/20; C40B 40/02; G01N 33/5005; G01N 33/543; G01N 33/5432; G01N 33/60; G01N 2333/195; G01N 2333/37; G01N 2333/405; G01N 2333/415; G01N 2500/00; G01N 33/5011; G01N 33/5014; G01N 33/502; G01N 33/5023; C12P 21/02; C12P 23/00; C07K 16/00; C07K 14/415; Y02A 90/10; Y02A 90/26; A01G 33/00; A23L 2/52; A23L 33/105; A61K 36/14; A61K 36/45; A61K 36/51; A61K 36/63; A61K 36/87; A61K 36/889; A61K 8/9722; A61K 8/9728; A61K 8/9767; A61K 8/9789; A61K 8/9794; A61P 35/00; A61P 39/00; A61P 39/06; A61Q 19/00; C12M 21/02; C12M 35/02; A01H 3/00
See application file for complete search history.

(56) References Cited

U.S. PATENT DOCUMENTS

| | | | |
|---|---|---|---|
| 2014/0079639 A1* | 3/2014 | McDaniel | A61P 35/00 424/9.2 |
| 2015/0218254 A1* | 8/2015 | Sabbadini | G01N 33/5005 435/252.3 |

\* cited by examiner

*Primary Examiner* — Michelle F. Paguio Frising
(74) *Attorney, Agent, or Firm* — Nguyen Tarbet LLC

(57) ABSTRACT

Methods of enhancing biomass and secondary metabolite accumulation of microalgal species are described herein. A cell culture of the microalgal species were elicited using a combination of techniques for a period of time. Experimental studies compared biomass dry weight production, chlorophyll dry weight content and astaxanthin dry weight content between controls and elicitation treatments. The present invention demonstrated that combined elicitation is an effective method for improving cell biomass growth and astaxanthin production.

11 Claims, 7 Drawing Sheets
(4 of 7 Drawing Sheet(s) Filed in Color)

| Cells phase | | Initial inoculum | Biomass production[c] | Basal level of astaxanthin concentration | Astaxanthin concentration[a] | Basal level of chlorophyll concentration | Chlorophyll concentration[b] |
|---|---|---|---|---|---|---|---|
| Exponential | Wild-type[d] | 0.367 ± 0.004 | 0.260 ± 0.001 | 2.898 ± 0.015 | 2.800 ± 0.038 | 36.541 ± 0.537 | 26.424 ± 0.033 |
| | N starvation[e] | 0.358 ± 0.002 | 0.319 ± 0.006 | 2.792 ± 0.047 | 4.512 ± 0.078 | 38.260 ± 0.595 | 35.975 ± 0.770 |
| | 60 mins EE[f] | 0.363 ± 0.011 | 0.438 ± 0.011 | 2.860 ± 0.081 | 1.939 ± 0.063 | 37.290 ± 1.043 | 21.297 ± 0.473 |
| | 30 mins EE | 0.358 ± 0.005 | 0.304 ± 0.011 | 2.800 ± 0.043 | 2.551 ± 0.044 | 38.028 ± 0.661 | 26.350 ± 0.928 |
| | 10 mins EE | 0.348 ± 0.019 | 0.241 ± 0.012 | 2.922 ± 0.102 | 1.922 ± 0.202 | 39.909 ± 2.043 | 19.615 ± 0.915 |
| | 60 mins EE + N[g] | 0.359 ± 0.011 | 0.340 ± 0.008 | 2.958 ± 0.097 | 2.737 ± 0.115 | 38.889 ± 1.329 | 34.516 ± 0.774 |
| | 30 mins EE + N | 0.352 ± 0.010 | 0.306 ± 0.008 | 2.972 ± 0.160 | 3.608 ± 0.135 | 39.173 ± 0.991 | 37.963 ± 0.983 |
| | 10 mins EE + N | 0.364 ± 0.011 | 0.329 ± 0.009 | 2.808 ± 0.041 | 4.355 ± 0.142 | 37.942 ± 1.186 | 36.333 ± 1.055 |
| Stationary | Wild-type | 0.354 ± 0.003 | 0.334 ± 0.005 | 4.422 ± 0.001 | 2.263 ± 0.038 | 34.983 ± 0.318 | 20.678 ± 0.368 |
| | N starvation | 0.347 ± 0.009 | 0.401 ± 0.013 | 4.609 ± 0.163 | 5.257 ± 0.149 | 36.212 ± 0.909 | 31.073 ± 1.387 |
| | 60 mins EE | 0.361 ± 0.003 | 0.342 ± 0.006 | 4.383 ± 0.037 | 1.552 ± 0.024 | 33.942 ± 0.229 | 17.860 ± 0.291 |
| | 30 mins EE | 0.348 ± 0.005 | 0.349 ± 0.008 | 4.804 ± 0.081 | 2.148 ± 0.065 | 36.175 ± 0.588 | 30.132 ± 0.533 |
| | 10 mins EE | 0.349 ± 0.003 | 0.331 ± 0.009 | 4.488 ± 0.042 | 2.454 ± 0.044 | 36.340 ± 0.107 | 23.054 ± 0.872 |
| | 60 mins EE + N | 0.349 ± 0.004 | 0.356 ± 0.013 | 4.576 ± 0.044 | 3.856 ± 0.105 | 35.301 ± 0.454 | 34.396 ± 1.327 |
| | 30 mins EE + N | 0.355 ± 0.006 | 0.351 ± 0.008 | 4.459 ± 0.085 | 5.305 ± 0.185 | 34.949 ± 0.548 | 34.424 ± 0.794 |
| | 10 mins EE + N | 0.347 ± 0.006 | 0.331 ± 0.006 | 4.623 ± 0.078 | 5.937 ± 0.060 | 36.143 ± 0.730 | 37.201 ± 0.608 |

[a] Average astaxanthin dry weight concentration (mg g⁻¹) in day 12. [b] Average chlorophyll dry weight concentration (mg g⁻¹) in day 12.
[c] Average biomass dry weight production (g L⁻¹) in day 12. [d] Wild-type non-elicited control. [e] Nitrogen starvation astaxanthin-producing positive control. [f] EE: Electrical elicitation treatment. [g] EE + N: Electrical elicitation plus nitrogen starvation treatment

FIG. 1

| Cells phase | Treatments | Percentage change as compared with Wild-type | | | Percentage change as compared with N starvation | | | Percentage change as compared with its basal level | | |
|---|---|---|---|---|---|---|---|---|---|---|
| | | Astaxanthin concentration[a] | Chlorophyll concentration[b] | Biomass production[c] | Astaxanthin concentration | Chlorophyll concentration | Biomass production | Astaxanthin concentration | Chlorophyll concentration | Biomass production |
| Exponential | Wild-type[d] | - | - | - | ↑ 37.95% | ↑ 26.53% | ↓ 18.59% | ↓ 3.39% | ↓ 27.67% | ↓ 29.27% |
| | N starvation[e] | ↑ 61.15% | ↑ 36.15% | ↑ 22.84% | - | - | - | ↑ 61.61% | ↓ 5.97% | ↓ 10.95% |
| | 60 mins EE[f] | ↓ 30.74% | ↓ 19.40% | ↑ 68.78% | ↑ 57.02% | ↓ 40.80% | ↑ 37.40% | ↑ 32.20% | ↓ 42.89% | ↑ 26.62% |
| | 30 mins EE | ↓ 8.97% | NSD | ↑ 17.17% | ↓ 43.45% | ↓ 26.75% | NSD | ↓ 8.86% | ↓ 30.71% | ↓ 15.00% |
| | 10 mins EE | ↓ 31.37% | ↓ 25.77% | NSD | ↓ 57.41% | ↓ 45.48% | ↓ 24.35% | ↓ 34.23% | ↓ 50.85% | ↓ 30.62% |
| | 60 mins EE + N[g] | NSD | ↑ 30.62% | ↑ 30.77% | ↓ 35.35% | NSD | ↑ 6.45% | NSD | ↓ 11.24% | NSD |
| | 30 mins EE + N | ↑ 29.88% | ↑ 43.67% | ↑ 17.79% | ↓ 20.02% | NSD | NSD | ↑ 21.41% | NSD | ↓ 19.16% |
| | 10 mins EE + N | ↑ 55.54% | ↑ 37.50% | ↑ 26.58% | NSD | NSD | NSD | ↑ 55.05% | NSD | ↓ 9.65% |
| Stationary | Wild-type | - | - | - | ↓ 56.95% | ↓ 33.45% | ↓ 16.61% | ↓ 48.82% | ↓ 40.89% | ↓ 5.55% |
| | N starvation | ↑ 132.29% | ↑ 50.27% | ↑ 19.92% | - | - | - | ↑ 14.06% | ↓ 14.19% | ↑ 15.54% |
| | 60 mins EE | ↓ 31.42% | ↓ 13.63% | NSD | ↓ 70.48% | ↓ 42.52% | ↓ 14.75% | ↑ 64.59% | ↓ 47.38% | ↓ 5.33% |
| | 30 mins EE | ↓ 5.09% | ↑ 45.72% | NSD | ↓ 59.14% | NSD | ↓ 12.93% | ↓ 53.34% | ↓ 16.70% | NSD |
| | 10 mins EE | ↑ 9.41% | ↑ 11.49% | NSD | ↓ 53.33% | ↓ 25.81% | ↓ 17.48% | ↓ 45.32% | ↓ 36.56% | NSD |
| | 60 mins EE + N | ↑ 70.35% | ↑ 66.34% | ↑ 6.49% | ↓ 26.65% | ↑ 10.69% | ↑ 11.26% | ↓ 15.73% | NSD | NSD |
| | 30 mins EE + N | ↑ 134.38% | ↑ 66.46% | ↑ 4.96% | NSD | ↑ 10.76% | ↓ 12.53% | ↑ 18.96% | NSD | NSD |
| | 10 mins EE + N | ↑ 162.31% | ↑ 79.90% | NSD | ↑ 12.92% | ↑ 19.72% | ↓ 17.37% | ↑ 28.43% | NSD | NSD |

[a] Average astaxanthin dry weight concentration (mg g$^{-1}$) in day 12. [b] Average chlorophyll dry weight concentration (mg g$^{-1}$) in day 12. [c] Average biomass dry weight production (g L$^{-1}$) in day 12. [d] Wild-type non-elicited control. [e] Nitrogen starvation astaxanthin-producing positive control. [f] EE: Electrical elicitation treatment. [g] EE + N: Electrical elicitation plus nitrogen starvation treatment. [h] NSD: no significant difference. [i] basal level: the initial measured value from each treatment in day 0.

FIG. 2

COMBINED ELICITATION FOR ENHANCEMENT OF CELL GROWTH AND PRODUCTION OF SECONDARY METABOLITES IN MICROALGAE CULTURES

CROSS-REFERENCES TO RELATED APPLICATIONS

This application is a non-provisional and claims benefit of U.S. Provisional Application No. 62/768,509 filed Nov. 16, 2018, the specification(s) of which is/are incorporated herein in their entirety by reference.

BACKGROUND OF THE INVENTION (1) Field of the Invention

The present invention relates to microalgal cell cultures and production of secondary metabolites therefrom, namely, combined elicitation may enhance biomass accumulation of *Haematococcus pluvialis* cells and other microalgal species during the exponential vegetative growth phase. Further, combined elicitation may enhance astaxanthin accumulation in *H. pluvialis* cells and various types of secondary metabolites in other microalgal species during the growth saturation phase.

(2) Description of Related Art Including Information Disclosed

*Haematococcus pluvialis* is a photoautotrophic microalgal species that has emerged as a leading producer of the secondary metabolite astaxanthin, an antioxidant pigment, under different biotic or abiotic stress conditions. The commercial value of astaxanthin encompasses applications in nutraceutical, pharmaceutical and aquaculture industries. In favorable conditions, *H. pluvialis* cells are green and motile, and may undergo morphologic and metabolic changes from green cells to red immobile cells as a response to stress conditions, resulting in the accumulation of astaxanthin mainly in the red phase. As a result, *H. pluvialis* is capable of overproducing and accumulating large quantities of ketocarotenoid astaxanthin up to 5% dry weight under unfavorable or stress-inducing environmental or culture conditions, such as nutrient deprivation, increased photon irradiance, increased salinity, high/low temperature, and combinations of stress factors. All these are known to accelerate astaxanthin synthesis and accumulation.

The synthesis of high amounts of astaxanthin, produced by stress conditions, can enhance the cell resistance to oxidative damage. The overproduction of oxidative molecules may induce protein, lipid and DNA oxidation, and thus cause deleterious effects on cells. Astaxanthin displays high antioxidant activity, allowing this molecule to provide effective protection from free radicals by quenching of oxygen atoms. Therefore, astaxanthin synthesis corresponds to a multifunctional response to stress environment or culture conditions.

Plant cells produce and accumulate various secondary metabolites, facilitating them to adapt and overcome in response to diverse environmental stresses. These stress conditions that stimulate and induce defensive response from plants have been defined as "elicitors". Elicitors are able to induce physiological responses and secondary metabolites production in plants and may be classified as follows (i) abiotic elicitors, such as UV light, heavy metals, high hydrostatic pressure, which are chemicals or physical stimuli; (ii) biotic elicitors, such as bacteria, virus or herbivore infections, which are of biological origin. During the past decade, numerous elicitor-mediated approaches have been developed and established to enhance the production and accumulation of various secondary metabolites in plant cultures. However, the challenges and disadvantages of typical abiotic and biotic elicitors were also observed, which included the negative effects on the physiological properties of plant cells as well as the difficulty of removing or separating the elicitor from the hard to separate compounds of interest. Hence, there is a need for improved methods of eliciting secondary metabolites.

BRIEF SUMMARY OF THE INVENTION

It is an objective of the present invention to provide a new approach to enhance astaxanthin production and/or improve growth in algae cell biomass using combined elicitation, as specified in the independent claims. Embodiments of the invention are given in the dependent claims. Embodiments of the present invention can be freely combined with each other if they are not mutually exclusive.

In some aspects, the present invention provides a method of enhancing secondary metabolite accumulation in a microalgal cell culture. The method may comprise exposing the microalgal cell culture to a combination of elicitors. Without wishing to limit the present invention, it is believed that combining elicitors can increase production of the secondary metabolite. The method may utilize abiotic (non-living) and biotic (living or derived from living) elicitors. Examples of abiotic elicitors include, but are not limited to, electrical elicitation, light quality (e.g., white, red, blue, UV, far red, etc.), intensity, and photoperiod, high and low temperatures, mechanical stresses such as agitation in a raceway or sonication, heavy metal exposure, nutrient deficiency such as nitrogen, phosphorus, sulfur, etc., or high or low salinity. Examples of biotic elicitors include, but are not limited to, fungi, bacteria, viruses, other species of algae, or components thereof.

One of the unique and inventive technical features of the present invention is the use of a combination of elicitors. Without wishing to limit the invention to any theory or mechanism, it is believed that the technical feature of the present invention advantageously provided at least an increase in secondary metabolite production, and in some cases, increased biomass production as well. None of the presently known prior references or work has the unique inventive technical feature of the present invention.

Previously, combining elicitors to elicit secondary metabolites from plant cells or algae cells has not been a practice or convention in the field, and was generally thought to be counter-intuitive. Elicitation of living cells is a significantly energy-demanding process for the cells, requiring that they channel their energy and material resources to the normally unnecessary synthesis of the secondary metabolites which, owing to their typically complex chemical structures, necessitate considerable energy expenditure. Introducing an elicitor to a cell culture causes a physical, physiological and biochemical shock to the cells. The elicitor incites the cells to quickly re-purpose and re-channel their energy and material resources toward the synthesis of certain secondary metabolites. If not properly regulated in terms of elicitor concentration or magnitude, this could very well result in cell death. Thus, conventional methods have been averse to working with combinations of elicitors given the challenging and precarious work involved with just one type of elicitor at any given time. However, the inventors have surprisingly found that combination of elicitors resulted in increased production of secondary metabolites.

According to another aspect, the strategy of electrical elicitation (EE) as an abiotic elicitor was applied for the first time to microalgal cells using *H. pluvialis* cell cultures. Instead of using *H. pluvialis* cells in the saturation growth phase, treatments of *H. pluvialis* green cells in the exponential vegetative growth phase were separately exposed to electrical current of 200 mA at three exposure time periods: 10 mins, 30 mins and 60 mins. The results showed the biomass dry weight production of $0.491\pm0.015$ g $L^{-1}$ and $0.435\pm0.015$ g $L^{-1}$ were obtained in the 60 mins and 30 mins EE treatments, respectively, after 12 days of cultivation. These represented increases of 44.1% and 27.6% for the two mentioned treatments, respectively, relative to the non-elicited control. Meanwhile, the chlorophyll and astaxanthin dry weight contents were significantly reduced in all EE treatments relative to the control.

Microscopic examination of the morphological characteristics of the cells showed no observable adverse effects in the EE treatments. Without wishing to limit the invention to any theory or mechanism, the foregoing results demonstrated that EE may serve as a physical external stimulus, which could easily be turned on and off at will, to enhance biomass accumulation of *H. pluvialis* cells. Thus, the EE strategy constitutes a novel protocol for improving the productivity of *H. pluvialis* biomass in scalable photobioreactors, and by extension that of the commercially valuable astaxanthin contained in the microalgal biomass. None of the presently known prior references or work has the unique inventive technical feature of the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

This patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIG. 1 is a table summary of basal level and overall of astaxanthin concentration, chlorophyll concentration and biomass production between control and each treatment.

FIG. 2 is a table summary of overall percentage changes of astaxanthin concentration, chlorophyll concentration and biomass production among all the treatments in day 12 between controls and basal level.

DETAILED DESCRIPTION OF THE INVENTION

Figure 3:
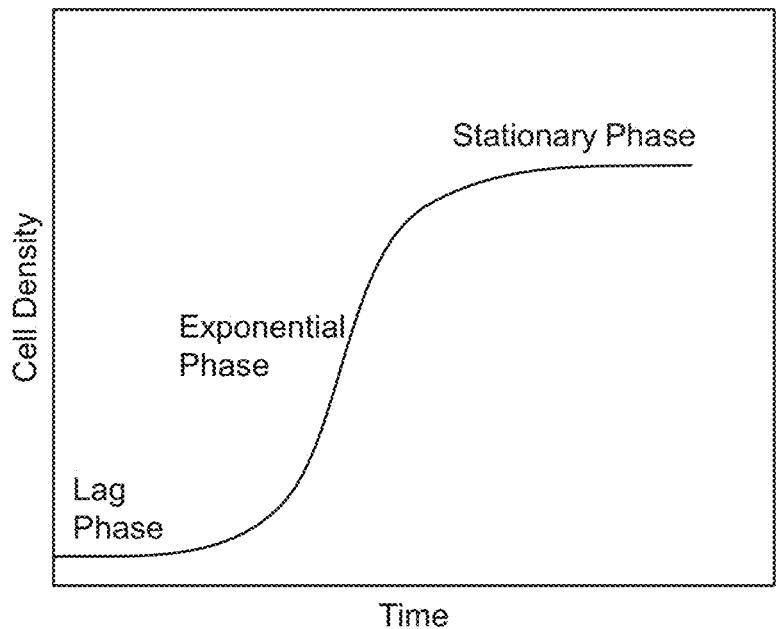
FIG. 3 shows a growth chart of a microalgae cell culture over time.

Referring now to the figures, in some embodiments, the present invention features a method of enhancing secondary metabolite accumulation in a microalgal cell culture. In one embodiment, the method may comprise electrically eliciting the microalgal cell culture by exposing said culture to sub-lethal levels of electric current for a period of time during a stationary growth phase of the microalgal cell culture, and depriving the microalgal cell culture of nitrogen during the stationary growth phase. Without wishing to limit the present invention to a particular theory or mechanism, the combination of electrical elicitation and nitrogen deprivation can increase production of the secondary metabolite by the microalgal cell culture. In further embodiments, the method may also include electrically eliciting the microalgal cell culture during an exponential growth phase of the microalgal cell culture. FIG. 3 shows the growth phases of a microalgal cell culture.

According to another embodiment, the present invention features a method of enhancing secondary metabolite accumulation in a cell culture. The cell culture may comprise microalgal cells or plant cells. In some embodiments, the method may comprise exposing the cell culture to at least two elicitors. Without wishing to limit the present invention, it is believed that combining the at least two elicitors can increase production of the secondary metabolite. The number of elicitors may range from 2 to 4 elicitors. In other embodiments, the method may implement more than 4 elicitors.

In one embodiment, the cell culture may be exposed to the at least two elicitors during a stationary growth phase of the cell culture. For example, the cell culture may be exposed to electrical elicitation and nutrient deprivation during the stationary growth phase. In an alternative embodiment, the cell culture may be exposed to one elicitor during an exponential growth phase and then to another elicitor during the stationary growth phase. For example, the cell culture may be exposed to electrical elicitation during the exponential growth phase and then to nutrient deprivation during the stationary growth phase.

In another alternative embodiment, the cell culture is exposed to one elicitor during the exponential growth phase and then to at least two elicitors during the stationary growth phase of the cell culture. For example, the cell culture may be exposed to electrical elicitation during the exponential growth phase and then to electrical elicitation and nutrient deprivation during the stationary growth phase. Without wishing to limit the present invention to a particular theory or mechanism, this embodiment may enable increased biomass production during the exponential growth phase and increased production of the secondary metabolite during the stationary growth phase.

In some embodiments, the at least two elicitors may be abiotic elicitors, biotic elicitors, or a combination thereof. Examples of abiotic elicitors include, but are not limited to electrical elicitation, light elicitation, temperature variation, mechanical stress, heavy metals, nutrient deprivation, or low or high salinity. Non-limiting examples of biotic elicitors include fungi, bacteria, virus, other species of microalgae, or fragments thereof.

In one embodiment, light elicitation may comprise exposing the microalgal cell culture to white, red, blue, or ultraviolet light, infrared, or far red radiation. In another embodiment, the heavy metals may comprise mercury (Hg), cadmium (Cd), arsenic (As), chromium (Cr), thallium (TI), lead (Pb), or other types of heavy metals. In other embodiments, nutrient deficiency may comprise deficiency in nitrogen, phosphorus, sulfur, or other nutrients that are typically given to plants or algae cultures.

In some embodiments, the microalgal cell culture may comprise *Haematococcus pluvialis* cells. The secondary metabolite may be astaxanthin. However, the present invention is not limited to *H. pluvialis*. Other microalgal species may be used in accordance with the present invention to produce various types of secondary metabolites.

In some other embodiments, plant cells may be cultivated according to the methods described in the present invention to enhance or increase production or accumulation of secondary metabolites. Examples of such metabolites include, but are not limited to, terpenes, flavonoids, phenolics such as resveratrol, glycosides, and alkaloids.

In other embodiments, the present invention features a method of enhancing biomass accumulation of a microalgal cell culture. The method may comprise placing electrodes that are operatively coupled to a power source in the microalgal cell culture, and electrically eliciting the microalgal cell culture by exposing said culture to sub-lethal levels of electric current via the electrodes for a period of time. In some embodiments, the method is performed during an exponential vegetative growth phase of the microalgal cell culture. Without wishing to limit the invention to a particular theory or mechanism, the electrical elicitation of the microalgal cell culture may increase a biomass of said culture. This increase in biomass may further increase a concentration of secondary metabolites in the microalgal cells. For instance, the electrical elicitation of a microalgal cell culture comprised of *Haematococcus pluvialis* cells may increase a biomass of said culture, thereby increasing a concentration of astaxanthin in the *H. pluvialis* cells.

According to another embodiment, the present invention features a method of enhancing secondary metabolite accumulation in a microalgal cell culture by placing electrodes that are operatively coupled to a power source in the microalgal cell culture, and electrically eliciting the microalgal cell culture by exposing said culture to sub-lethal levels of electric current via the electrodes for a period of time. In some embodiments, the method is performed during a growth saturation phase of the microalgal cell culture. Without wishing to limit the present invention, the electrical elicitation of the microalgal cell culture may increase a concentration of the secondary metabolite in the microalgal cells. For instance, the electrical elicitation of a microalgal cell culture comprised of *Haematococcus pluvialis* cells may increase a concentration of astaxanthin in the *H. pluvialis* cells.

In conjunction with various methods described above, the methods may further comprise mixing the microalgal cell culture during electrical elicitation to prevent ionic gradients. The culture may be mixed using a mixer or paddle that causes circulation of the culture.

Figure 4:
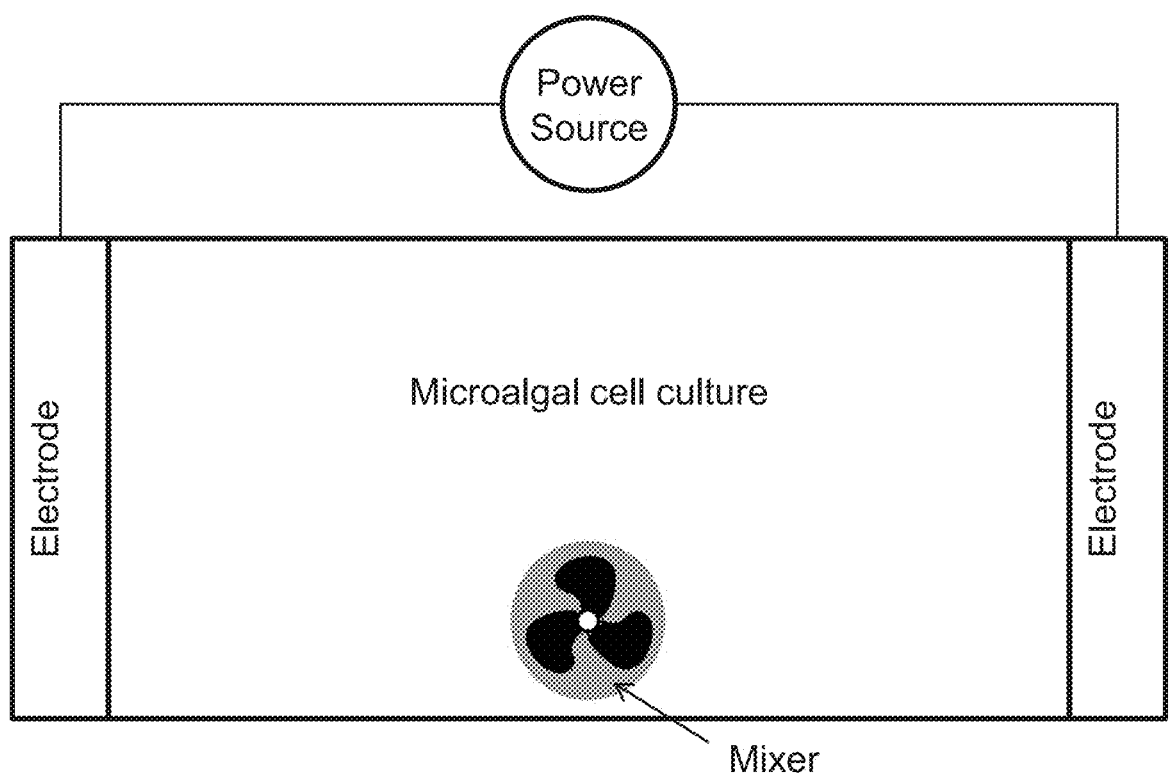
FIG. 4 is a non-limiting embodiment of an electrical elicitation (EE) schematic that may be used in accordance with the present invention.

In one embodiment, electrical elicitation may comprise placing electrodes in the microalgal cell culture. As shown in FIG. 4, the electrodes are operatively coupled to a power source, and the electrodes supply said sub-lethal levels of electric current. The sub-lethal levels of electric current may range from about 30 mA to about 400 mA of direct current or alternating current. For example, the current level may be about 100 mA, or 200 mA, or 300 mA, or other levels may be used. The optimal current level may also vary from species to species and depending on the culture conditions.

In some embodiments, the period of time for electrical elicitation can range from about 10 minutes to about 60 minutes. In other embodiments, the period of time for electrical elicitation ranges from about 10 minutes to about 30 minutes or about 30 minutes to about 1 hour. In yet other embodiments, the period of time for electrical elicitation is greater than 1 hour. In preferred embodiments, the methods may further comprise a cooling step during electrical elicitation to prevent overheating of the microalgal culture.

In other embodiments, the methods may further comprise incubating the microalgal cell culture after elicitation. In one embodiment, the microalgal cell culture may incubated under a light intensity of about 30 $\mu mol\ photons \cdot m^{-2} \cdot s^{-1}$. Other light intensities may be used, such as about 10-50 $\mu mol\ photons \cdot m^{-2} \cdot s^{-1}$. In another embodiment, the microalgal cell culture may be incubated under ultraviolet light.

In some embodiments, the microalgal cell culture may be cultivated for a period of about 10-20 days. During this cultivation period, the methods described herein may be repeated at least once per day. For example, the microalgal cell culture may undergo electrical elicitation once per day. As another example, the microalgal cell culture may undergo electrical elicitation twice per day or every other day.

Example 1

The following is a non-limiting example of implementing electrical elicitation in accordance with the present invention. It is to be understood that said example is not intended to limit the present invention in any way. Equivalents or substitutes are within the scope of the present invention.

Experimental

Culture Conditions of *H. pluvialis*

*H. pluvialis* cells were obtained from the Biophamia LLC, Norway. All the cells were cultured in modified OHM medium. The formula of modified OHM culture medium was provided by Biophamia LLC, and was listed as follows: 0.7482 mM $CaCl_2 \cdot 2H_2O$, 4.0552 mM $KNO_3$, 0.2113 mM $Na_2HPO_4$, 0.9981 mM $MgSO_4 \cdot 7H_2O$, 0.0451 $\mu M$ $SeO_2$, 3.4218 $\mu M$ EDTA, essential trace elements of 0.0117 mM $FeCl_3 \cdot 6H_2O$, 0.0117 mM $Na_2EDTA \cdot 2H_2O$, 0.0393 $\mu M$ $CuSO_4 \cdot 5H_2O$, 0.0260 $\mu M$ $Na_2MoO_4 \cdot 2H_2O$, 0.0765 $\mu M$ $ZnSO_4 \cdot 7H_2O$, 0.042 $\mu M$ $CoCl_2 \cdot 6H_2O$, 0.9100 $\mu M$ $MnCl_2 \cdot 4H_2O$ and vitamins of 0.296 $\mu M$ Thiamine HCl, 0.0021 $\mu M$ biotin and 0.369 nM $B_{12}$.

The *H. pluvialis* green vegetative cells with initial biomass dry weight $0.355 \pm 0.013\ g\ L^{-1}$ were cultured in several 1 L sterilized glass bottles under indoor conditions with continuous T8 fluorescent lamp of a photon flux density of 60 $\mu mol\ photons \cdot m^{-2} \cdot s^{-1}$ at 25° C. Culture mixing was circulated by normal air aeration through a sterilized thin glass tube with a connected 0.22 $\mu m$ syringe filter which was integrated on the top of glass bottles. These inoculums were grown for at least 7 days in modified OHM medium, then 200 ml of *H. pluvialis* cultivation were further cultured in a 250 ml Erlenmeyer flask after the cells reaches the exponential phase.

Observing *H. pluvialis* Cell Conditions by Optical Microscopy

*H. pluvialis* cells obtained from RBC and AAPBR were observed under an optical image system to visualize cell morphological change from green vegetative stage to red cyst stage. Images were captured with a ToupView software systems combined with binocular microscope (B100B-MS, Amscope, USA), a USB digital color camera (MU500-CK, Amscope, USA), and 400× Amscope achromatic microscope objective. The brightness, contrast and gamma value were further adjusted by ToupView software.

Electrical Elicitation Treatment for *H. pluvialis* Cells

The electrical elicitation procedure was as follows: 200 ml of modified OHM medium containing log-phase *H. pluvialis* fresh culture (~0.355±0.013 g $L^{-1}$ dry weight) was conducted with electrical current in a 400 ml glass beaker (PyREX, USA) that was 7.5 cm in diameter and 11.5 cm in height. A power supply unit (EC 500, E-C Apparatus, St. Petersburg, Fla.) was employed for providing electrical current. Two stainless steel metal plates with width of 4.7 cm and length of 5.4 cm served as electrodes and were connected to the power supply and were fixed at two opposite ends of the 400 ml glass beaker. Three *H. pluvialis* cultures were separately treated with 200 mA of DC (with voltage readings of 18-20 V) for 60 mins, 30 mins and 10 mins. In order to prevent overheating, the entire process was performed in a water bath at a constant temperature of 20° C. A magnetic stirrer was placed in each treatment and constantly stirred with the elicitation *H. pluvialis* cells containing medium to avoid the effect of ionic gradients across the electrodes. After the elicitation, the *H. pluvialis* culture were centrifuged for 10 mins at 4,000×g at 25° C. and transferred to a clean 250 ml Erlenmeyer flask, followed by incubating in a gyratory shaker (New Brunswick Scientific, Edison, N.J.) at 130 rpm with light intensity of 30 μmol photons· $M^{-2} \cdot s^{-1}$ at 25° C.

The Measurement of *H. pluvialis* Biomass Dry Weight

The biomass accumulation of *H. pluvialis* cells were measured by biomass dry weight. Whatman filter membrane with a diameter of 7.5 cm and 0.45 μm pore size was dried at 95° C. in an oven for 24 hours, and pre-weighted after cooling down to room temperature. Subsequently, 5 ml of liquid fresh cultures were separately taken every 24 hours, and filtered, dried and weighted with filter membranes following the same procedure. The biomass dry weight of each sample was determined by the difference between pre-weighted filter membrane and algae-containing filter membrane.

The Extraction and Measurement of Chlorophyll Contents

The procedure to extract total chlorophyll from *H. pluvialis* was as follows: Operating in dim light, 3 ml of cells were centrifuged for 5 mins at 8,000×g at 25° C. The pellets were washed twice with 1 ml of sterilized distilled deionized water, and subsequently re-suspended in pure DMSO. The mixture was heated at 70° C. for 10 mins and then centrifuged for 5 mins at 8,000×g at 25° C. Finally, the extraction was transferred into a new microcentrifuge tube. These procedures were repeated several times until the appearance of white pellet.

The absorbance of the chlorophyll DMSO extraction was measured with a spectrophotometer (USB4000, Ocean Optics, USA), and the total chlorophyll content was determined using the following equations:

$$C_a = 14.85 A^{664.9} - 5.14 A^{648.2} \quad (1)$$

$$C_b = 25.48 A^{648.2} - 7.36 A^{664.9} \quad (2)$$

$$C_{a+b} = 7.49 A^{664.9} + 20.34 A^{648.2} \quad (3)$$

where A indicates absorbance wavelength (nm), $C_a$ represents Chlorophyll$_a$, $C_b$ shows Chlorophyll$_b$, and Chlorophyll$_{a+b}$ serves as total chlorophyll. The unit of concentration was milligram per milliliter.

The Extraction and Measurement of Astaxanthin Contents

The astaxanthin extraction method was as follows: Operating in dim light, 3 ml *H. pluvialis* cells were centrifuged for 5 mins at 8,000×g at 25° C. To remove the chlorophyll, the collected cells were treated with 5% methanolic KOH at 70° C. for 5 mins, this step was repeated until the cell pellet became white. After centrifugation for 5 mins at 8,000×g at 25° C., the harvested cells were washed with 2 ml of sterilized distilled deionized water. Subsequently, the collected cells were further treated with 4 N hydrochloric acid at 70° C. for 2 mins, and then centrifuged and washed with 2 mL of sterilized distilled deionized water. The cell pellet was re-suspended in pure DMSO and then centrifuged at 5 mins at 8,000×g at 25° C. Finally, the supernatants were further processed for astaxanthin estimation.

The absorbance of astaxanthin DMSO extracts were determined with a spectrophotometer (USB4000, Ocean Optics, USA), and the astaxanthin content was calculated using the following equation:

$$\text{Astaxanthin} = 4.5 \times OD490 \times (V_a/V_b) \times f \quad (4)$$

where Astaxanthin is the astaxanthin concentration in milligram per liter. The $V_a/V_b$ ratio indicates the volume between the extract and sample, and f represents a dilution ratio.

Statistical Analysis

Samples from the experiment were measured three times. The difference in the variances of all the tests was verified by using F-test, showing variances on each test to be statistically similar. Therefore, a two-tailed Student's t-test with equal assumption was employed to compare the difference among all treatments. This statistical analysis of data was calculated in Microsoft Excel. The 95% and 99% significant levels were employed to determine significant differences in the level of collected data between control and treatments.

Results

Figure 5:
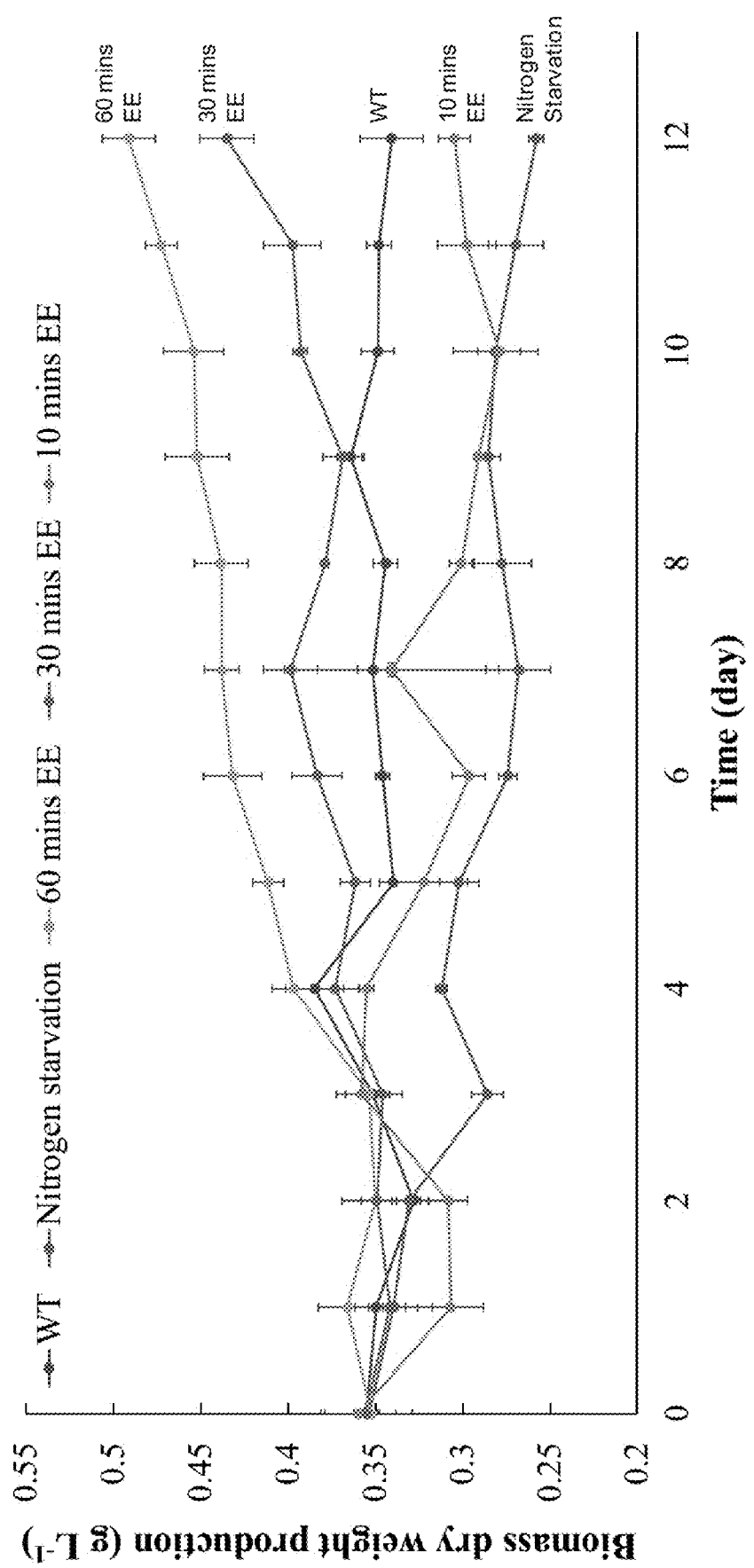
FIG. 5 shows a plot of biomass accumulation changes after EE treatments according to a non-limiting embodiment of the present invention.

Referring to FIG. 5, initial average astaxanthin dry weight content of *H. pluvialis* cells with average 1.920±0.075 mg $g^{-1}$ were separately treated with EE under different treatment times in day 0. Wild-type (WT) of *H. pluvialis* cells served as non-elicited control without performing any treatment, whereas the nitrogen starvation astaxanthin-producing positive control (N starvation) of *H. pluvialis* served as positive control, which was cultured under medium with no nitrogen source. 60 mins, 30 mins and 10 mins EE represented the different times of EE treatments. The astaxanthin accumulation was further observed for 12 days at 25° C. under 35 μmol photons·$m^{-2} \cdot s^{-1}$ of continuous fluorescent light. Each data point represents the mean of sample and error bar indicates standard deviation. "Black curve" and "red curve" indicates the internal and positive control, respectively. "Green, purple and blue curve' indicates the different EE treatments.

Figure 6:
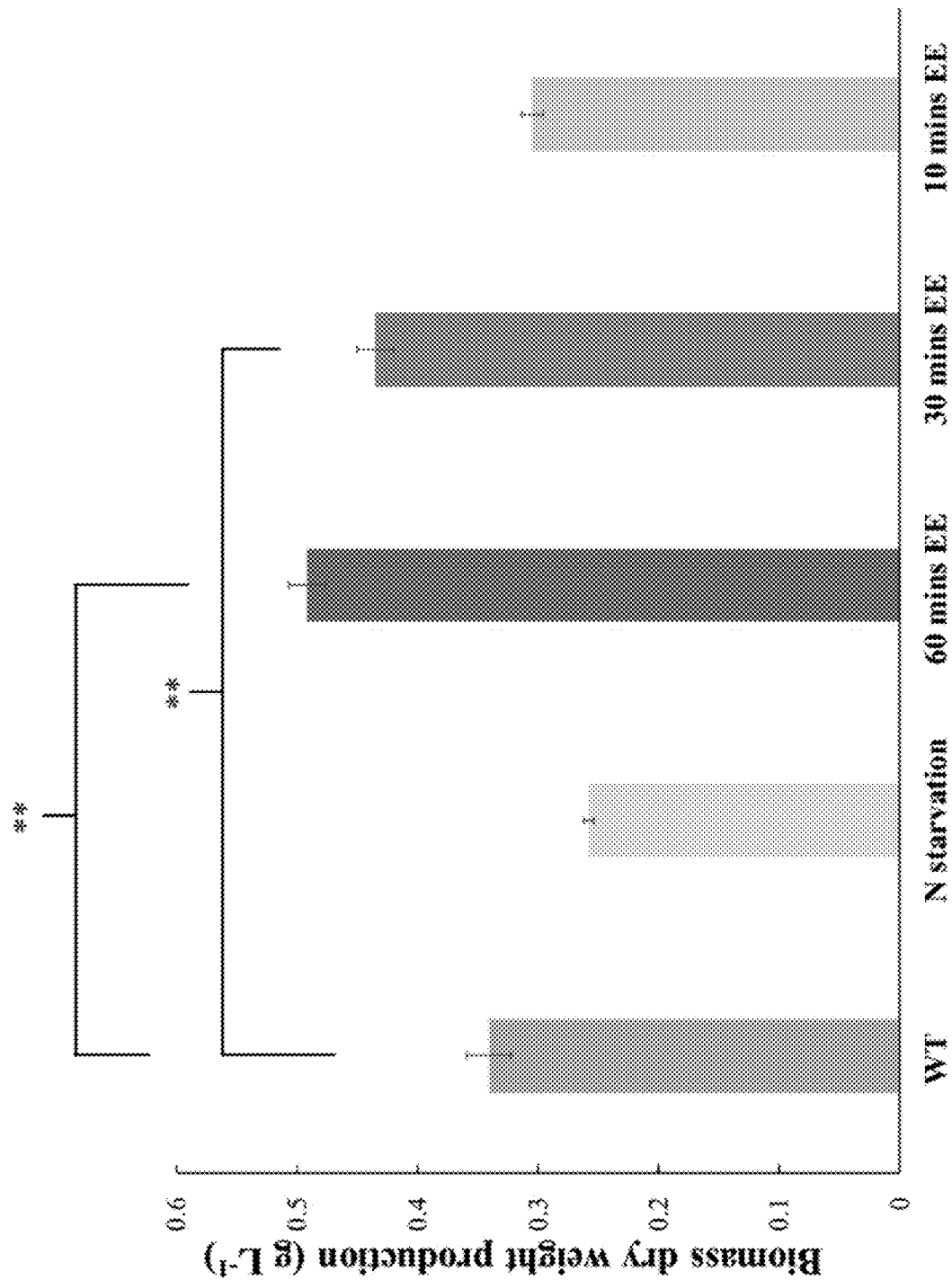
FIG. 6 is a plot showing the effects of EE treatments on biomass accumulation of *H. pluvialis*.

FIG. 6 shows the maximal astaxanthin dry weight content of *H. pluvialis* cultivation in day 12 under different treatments. Color on each column represents the amount of average biomass dry weight, as shown in dark green contained highest biomass. "EE" indicates electrical elicitation under different treatment times. Values are mean±standard deviation. Significant differences between WT and EE 30 mins were determined via Student's t-test, which was indicated by asterisks, as *P<0.05.

Figure 7:
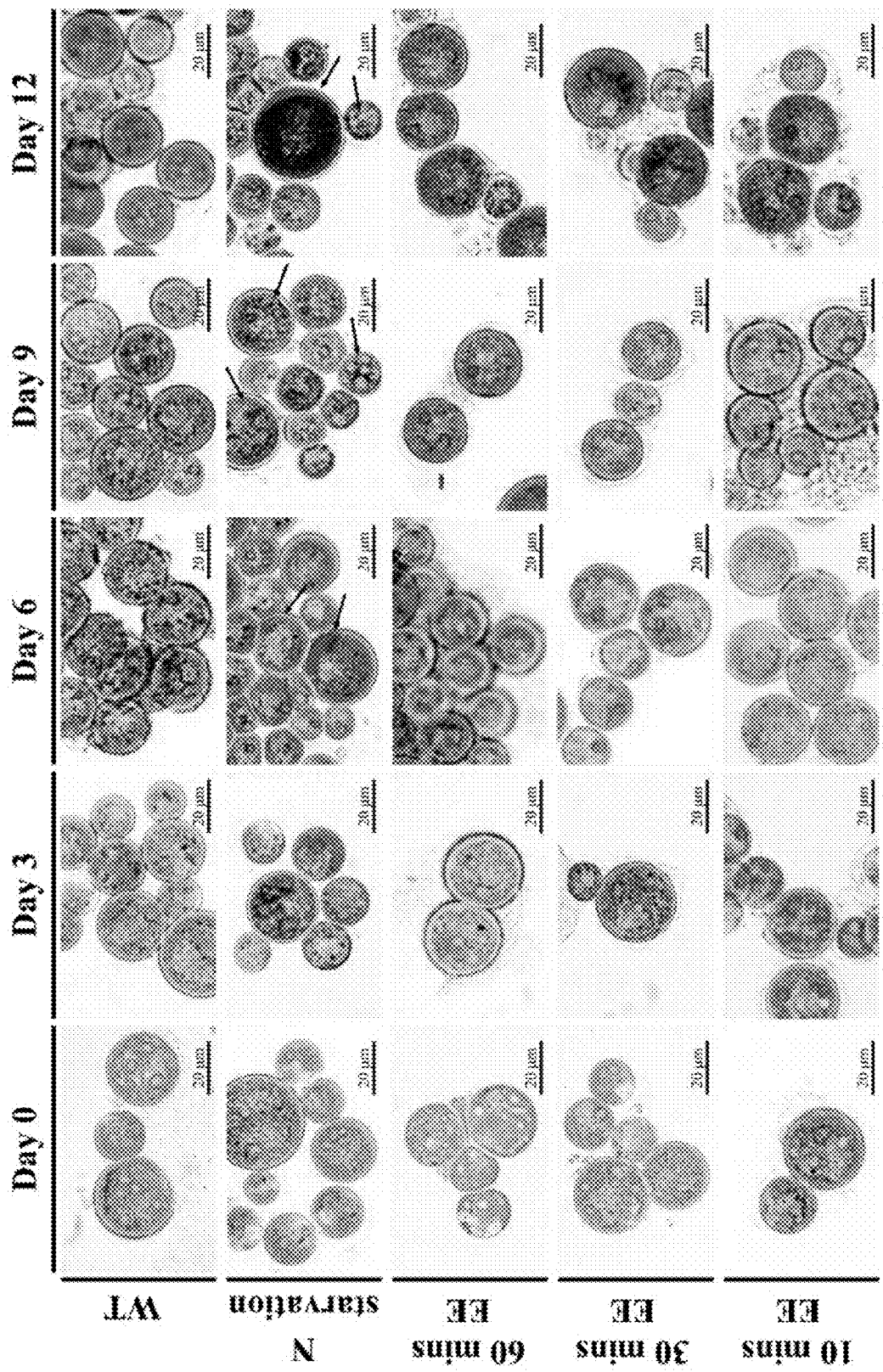
FIG. 7 shows visualization cell changes by optical microscopy imaging.

FIG. 7 is a visualization of EE and nitrogen starvation astaxanthin-producing positive control (N starvation) treated *H. pluvialis* cells by brightfield microscopy at 400× magnification. The constant green vegetative stage was observed in wild-type (WT) non-elicited control and EE treatments from day 1 to day 12. Red pigment accumulation occurred in N starvation in day 6, the bright reddish color presented by astaxanthin was observed within cells, as indicated by the black arrow. Scale bars: 20 μm.

Figure 8:
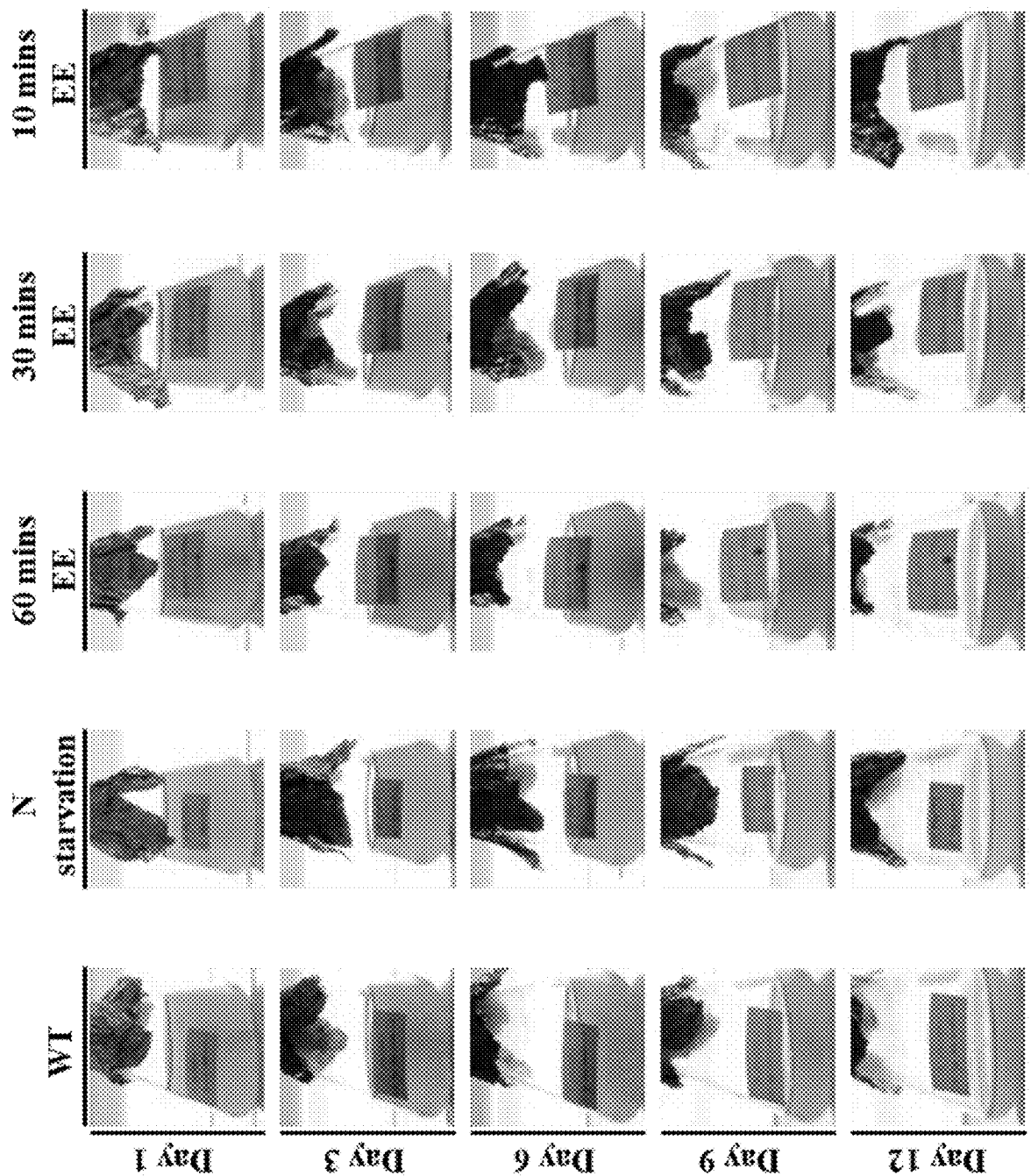
FIG. 8 shows images of *H. pluvialis* cultivation status under different treatments.

In FIG. 8, the pictures demonstrate the changes of *H. pluvialis* cultivation through day 1 to day 12 under effects of EE treatments. Wild-type (WT) and nitrogen starvation (N starvation) of *H. pluvialis* cells served as non-elicited control and astaxanthin-producing positive control, respectively.

Example 2

The following is a non-limiting example of implementing electrical elicitation, as described in the previous example, in combination with nitrogen starvation. It is to be understood that said example is not intended to limit the present invention in any way. Equivalents or substitutes are within the scope of the present invention.

Nitrogen Deprivation

Two 200-ml volumes of modified OHM medium each with *H. pluvialis* culture, one containing exponential-phase (~0.359±0.006 g $L^{-1}$ dry weight) and the other with stationary-phase culture (~0.351±0.005 g $L^{-1}$ dry weight), were separately treated with 200 mA DC (with voltage readings of 18-20 V) electrical current for 60 mins, 30 mins and 10 mins. After the elicitation, the *H. pluvialis* cultures at exponential or stationary phase were each centrifuged for 10 mins at 4,000×g at 25° C. and each transferred to a clean 250 ml Erlenmeyer flask containing 200 ml fresh OHM medium with no nitrogen source, followed by incubation on a New Brunswick (New Brunswick Scientific, Edison, N.J.) gyratory shaker at 130 rpm with a light intensity of 30 μmol photons $m^{-2}s^{-1}$ at 25° C. for 12 days.

Results

Astaxanthin

For the comparison and confirmation of astaxanthin accumulation, the final average astaxanthin dry weight concentration of all the treatments was compared with wild-type non-elicited control and nitrogen starvation astaxanthin-producing positive control of *H. pluvialis* cells at exponential phase at day 12 (FIGS. 1 and 2). Referring to FIG. 1, the wild-type non-elicited control accumulated an average of 2.800±0.038 mg $g^{-1}$ astaxanthin dry weight concentration in day 12. Meanwhile, the average astaxanthin dry weight concentration in nitrogen starvation astaxanthin-producing positive control displayed the highest average of 4.512±0.078 mg $g^{-1}$ astaxanthin dry weight concentration among all the treatments. It produced and accumulated average astaxanthin dry weight concentration up to 61.15% higher than that of wild-type non-elicited control. Both 30 mins and 60 mins EE treatments showed similar average astaxanthin dry weight content of 2.551±0.044 mg $g^{-1}$ and 1.939±0.063 mg $g^{-1}$, which were 17.90% and 30.74% less than wild-type non-elicited control, respectively. Among the EE treatments, the 10 mins EE exhibited the lowest average of 1.922±0.202 mg $g^{-1}$ astaxanthin dry weight concentration, which was 31.37% lower as compared to wild-type non-elicited control. In contrast, the average astaxanthin dry weight concentration of 3.608±0.135 mg $g^{-1}$ and 2.737±0.115 mg $g^{-1}$ were obtained in both 30 mins and 60 mins plus N treatments, which were 20.02% and 39.35% less than that of nitrogen starvation astaxanthin-producing positive control, respectively. Different from the reduction of average astaxanthin dry weight concentration, 10 mins plus N treatment displayed an average astaxanthin dry weight concentration of 4.355±0.142 mg $g^{-1}$, which had no statistical difference compare to nitrogen starvation astaxanthin-producing positive control. As a result, unlike nitrogen starvation astaxanthin-producing positive control, the average astaxanthin dry weight concentration with EE treatments was lower than wild-type non-elicited control. Likewise, the average astaxanthin dry weight concentration found in EE plus N treatments was lower than that observed in nitrogen starvation astaxanthin-producing positive control, indicating that the EE treatment was unable to perform as a physical elicitor to induce the astaxanthin production in *H. pluvialis* cells at exponential phase.

Despite the average astaxanthin dry weight concentration of all EE and EE plus N treatments of *H. pluvialis* cells being reduced at exponential phase some treatments of *H. pluvialis* cells at stationary phase continued to accumulate in astaxanthin concentration well beyond the concentration when the astaxanthin dry weight concentration had decreased. The average astaxanthin dry weight concentration with 2.263±0.038 mg $g^{-1}$ was found in wild-type non-elicited control (FIG. 1). Simultaneously, the average astaxanthin dry weight concentration in nitrogen starvation astaxanthin-producing positive control exhibited an average of 5.257±0.149 mg $g^{-1}$ astaxanthin dry weight concentration, which was 132.29% higher than that of wild-type non-elicited control (FIG. 2). The 60 mins EE treatment accumulated average astaxanthin dry weight concentration was 1.552±0.024 mg $g^{-1}$, a reduction in average astaxanthin dry weight concentration up to 31.42% as compared to wild-type non-elicited control. Meanwhile, an average astaxanthin dry weight concentration of 2.148±0.065 mg $g^{-1}$ was obtained for 30 mins EE treatment, yet it had no statistical difference compared to wild-type non-elicited control (FIG. 2). Conversely, in the 10 mins EE treatment the average astaxanthin dry weight concentration with 2.454±0.044 mg $g^{-1}$ displayed a higher concentration, which was a 8.41% enhancement than that of wild-type non-elicited control; however, it was still lower than the astaxanthin level in day 0 (FIG. 1). Compared to EE treatments of *H. pluvialis* at stationary phase, the EE plus N treatments caused different results on the accumulation of average astaxanthin dry weight concentration. Although an average astaxanthin dry weight concentration of 3.856±0.105 mg $g^{-1}$ was found in 60 mins EE plus N treatment, a 26.65% reduction was observed as compared to nitrogen starvation astaxanthin-producing positive control. The astaxanthin dry weight concentration of 5.305±0.165 mg $g^{-1}$ was observed under 30 mins EE plus N treatments, which corresponded to no statistical difference when compared to nitrogen starvation astaxanthin-producing positive control (FIG. 2). A maximum concentration of 5.937±0.060 mg $g^{-1}$ was obtained in 10 mins EE plus N treatments on *H. pluvialis* cells at stationary phase, which was much higher than the nitrogen starvation astaxanthin-producing positive control of 5.257±0.149 mg $g^{-1}$, demonstrating an overall 12.92% enhancement of astaxanthin accumulation. Furthermore, the average astaxanthin dry weight concentration in day 12 shows an improvement of up to 28.43% compared to day 0 (FIG. 2). These results suggest that astaxanthin accumulation is associated with EE and EE plus nitrogen starvation treatments and *H. pluvialis* cell phase, with the maximum improvement of average astaxanthin dry weight concentration being obtained from stationary phase *H. pluvialis* cells while processing under EE plus N treatment.

Biomass

The maximal average biomass dry weight with 0.438±0.011 g $L^{-1}$ was obtained in 60 mins EE treatment in day 12, demonstrating a 67.78% enhancement than that of 0.260±0.001 g $L^{-1}$ in wild-type non-elicited control (FIGS. 1 and 2). It accumulated biomass dry weight production up to 20.62% than its original level in day 0. The overall average biomass dry weight production in 30 mins EE treatment was improved as compared to wild-type non-elicited control in day 12. It exhibited an average biomass dry weight of 0.304±0.011 g $L^{-1}$, a 17.17% increase compared to the wild-type non-elicited control, yet this result was less than the average biomass dry weight in 30 mins EE treatment in day 0 (Table 1). Additionally, nitrogen starvation astaxanthin-producing positive control treatment exhibited higher average biomass dry weight production of 0.319±0.006 g $L^{-1}$ as expected owing to its accumulated astaxanthin to increase the survival rate of *H. pluvialis* cells, thus it displayed a higher average biomass dry weight production compared to wild-type non-elicited control. However, the overall average biomass dry weight of nitrogen starvation astaxanthin-producing positive control was still lower than its original biomass production in day 0 (Table 1). The 10 mins EE treatment displayed an opposing result from 60 mins and 30 mins EE treatments as described above, showing an average biomass dry weight of 0.241±0.012 g $L^{-1}$. As compared to wild-type non-elicited control, 10 mins EE treatment showed a 7.07% reduction of average biomass dry weight production. Results from these EE treatments suggest that the 60 mins EE may improve the biomass accumulation rate in the *H. pluvialis* cells at exponential phase. Similar to the results found in 10 mins EE treatment, the 60 mins EE plus N treatment displayed a decline of average biomass dry weight production as well. It showed an average biomass dry weight production with 0.340±0.008 g $L^{-1}$, which was 4.06% lower than that of the nitrogen starvation astaxanthin-producing positive control. The 10 mins and 30 mins EE plus N treatments accumulated average biomass dry weight with 0.329±0.008 g $L^{-1}$ and 0.340±0.008 g $L^{-1}$, respectively. Both treatments produced average biomass dry weight production up to 0.99% and 5.52% higher as compared to nitrogen starvation astaxanthin-producing positive control, whereas the overall biomass in day 12 was still lower than in day 0 (Table 1 and 2). Therefore, these results suggest that average biomass dry weight production was unable to be improved while conducting EE under the nitrogen starvation conditions. Taken together, as a result, only 60 mins EE treatments demonstrated that it was capable of improving the growth of *H. pluvialis* cultivation at exponential phase, allowing the biomass to accumulate continuously after conducted with EE treatment.

No average biomass dry weight production was improved in the *H. pluvialis* cells at stationary phase while conduction EE and EE plus N treatments. The wild-type non-elicited control accumulated a 0.334±0.005 g $L^{-1}$ average biomass dry weight production, showing a slightly decline of the biomass production compared to day 0 (Table 1). Meanwhile, the nitrogen starvation astaxanthin-producing positive control exhibited improvement of average biomass dry weight production with 0.401±0.013 g $L^{-1}$ in day 12 which was improved as compared with biomass production in day 0 due to protection of *H. pluvialis* cells against the oxidative damage. Therefore, it produced and accumulated average biomass dry weight production up to 19.92% higher than that of wild-type non-elicited control (Table 2). Meanwhile, 10 mins, 30 mins and 60 mins EE treatments displayed biomass dry weight production with 0.331±0.009 g $L^{-1}$, 0.349±0.008 g $L^{-1}$ and 0.342±0.006 g $L^{-1}$ in day 12, respectively (Table 1). Results showed that EE had almost no difference among all the EE treatments compared to the wild-type non-elicited control, indicating that a higher basal level of astaxanthin accumulated in cells at stationary phase may mitigate the negative influence on the biomass accumulation on the *H. pluvialis* carried by EE. In contrast, all the EE plus N treatments displayed a lower average biomass dry weight production than that of the nitrogen starvation astaxanthin-producing positive control in day 12. Similar biomass dry weight productions with 0.351±0.008 g $L^{-1}$ and 0.356±0.013 g $L^{-1}$ were observed in both 30 mins and 60 mins plus N treatments, which were 12.53% and 11.20% less than that of nitrogen starvation astaxanthin-producing positive control, respectively (Table 1 and 2). Unlike other EE plus N treatments, 10 mins EE plus N treatment displayed the lowest average biomass dry weight production with 0.331±0.006 g $L^{-1}$ in day 12, demonstrating a 17.37% reduction of biomass compared to nitrogen starvation astaxanthin-producing positive control. Therefore, results from EE plus N treatments revealed that EE coupled with nitrogen starvation may inhibit the biomass accumulation in *H. pluvialis* cells. Taken together among the EE and EE plus N treatments, it suggests that the EE was unable to serve as a physical elicitor to induce the biomass accumulation in *H. pluvialis* cells at stationary phase.

Chlorophyll

The final average chlorophyll dry weight concentration of all the treatments was compared with wild-type non-elicited control and nitrogen starvation astaxanthin-producing positive control from exponential phase *H. pluvialis* cells at day 12. The wild-type non-elicited control had an average chlorophyll dry weight concentration of 26.424±0.033 mg $g^{-1}$ at day 12, which was less than 36.541±0.537 mg $g^{-1}$ at day 0 (Table 1). Meanwhile, the nitrogen starvation astaxanthin-producing positive control treatment exhibited average chlorophyll dry weight concentration of 35.975±0.033 mg $g^{-1}$ at day 12. Compared to the average chlorophyll dry weight concentration of 38.260±0.595 mg $g^{-1}$ at day 0, it indicates that nitrogen starvation astaxanthin-producing positive control demonstrated a slightly reduction of the average chlorophyll dry weight concentration following the production with astaxanthin. In contrast, 30 mins EE treatment displayed an average chlorophyll dry weight concentration of 26.350±0.928 mg $g^{-1}$ at day 12, showing a similar final chlorophyll levels as compared to wild-type non-elicited control. Furthermore, an average chlorophyll dry weight concentration of 24.297±0.473 mg $g^{-1}$ was obtained in 60 mins EE treatments at day 12. Compared to wild-type non-elicited control, it demonstrated a reduction of chlorophyll level up to 19.40% (Table 2). Interestingly, 10 mins EE treatment displayed the lowest average chlorophyll concentration with 19.615±0.915 mg $g^{-1}$ at day 12, which was 25.77% less than that of wild-type non-elicited control. EE plus N treatments resulted in 37.963±0.928 mg $g^{-1}$, 36.333±1.055 mg $g^{-1}$, and 34.516±0.774 mg $g^{-1}$ for 10 mins, 30 mins and 60 mins EE plus N treatments, respectively, showing almost no change in average chlorophyll dry weight concentration as compared to the nitrogen starvation astaxanthin-producing positive control in day 12 (Table 2). Additionally, the average chlorophyll dry weight concentration in both 10 mins and 30 mins EE plus N treatments in day 12 were almost identical to day 0 (Table 1). Conversely, 60 mins EE plus N treatment displayed a decline of average chlorophyll dry weight concentration at day 12 as compared to day 0 (Table 2). Taken together, 10 mins, 30 mins, and 60 mins EE plus N treatment showed a reduction in chlorophyll levels as compared to controls, indicating that the EE under a specific plus length of time may have had a negatively influence on the production of chlorophyll dry weight concentration of *H. pluvialis* cells at exponential phase.

The effect of alternating the final average chlorophyll dry weight concentration by all the EE and EE plus N treatments of *H. pluvialis* cells at stationary phase was also investigated. The average chlorophyll dry weight concentration with 20.678±0.368 mg g$^{-1}$ and 31.073±1.387 mg g$^{-1}$ were found in both wild-type non-elicited control and nitrogen starvation astaxanthin-producing positive control at day 12, which were less than that of 34.983±0.318 mg g$^{-1}$ and 36.212±0.909 mg g$^{-1}$ in day 0 due to the accumulation of astaxanthin, respectively (Table 1). Meanwhile, 60 mins EE treatment displayed an average chlorophyll dry weight concentration of 17.860±0.291 mg g$^{-1}$, showing a 13.63% reduction of chlorophyll level as compared to wild-type non-elicited control. Conversely, both 10 mins and 30 mins EE treatments displayed average chlorophyll dry weight concentrations with 23.054±0.872 mg g$^{-1}$ and 30.132±0.533 mg g$^{-1}$ at day 12, which were 11.49% and 45.72% improvements of chlorophyll concentration when compared to wild-type non-elicited control, respectively. Nevertheless, compared to day 0, a decline of average chlorophyll dry weight concentration in day 12 was observed in 10 mins and 30 mins EE treatments (Table 2). The average chlorophyll dry weight concentrations were improved by the EE plus N treatments of *H. pluvialis* cells at stationary phase as compared to nitrogen starvation astaxanthin-producing positive control. 10, 30 and 60 mins EE plus N treatments maintained an average chlorophyll dry weight concentration of 34.424±0.794 mg g$^{-1}$, 34.396±1.327 mg g$^{-1}$ and 37.201±0.608 mg g$^{-1}$ at day 12, respectively. Compared to its average chlorophyll dry weight concentration from day 0, almost no change in chlorophyll levels were found in all EE plus N treatments (Table 2). Nevertheless, both treatments still showed 10.78% and 10.69% improvement of chlorophyll level than that of nitrogen starvation astaxanthin-producing positive control at day 12. Interestingly, 10 mins plus N treatment exhibited the highest average chlorophyll dry weight concentration at day 12 among all treatments, which was a 19.72% enhancement of chlorophyll level as compared to nitrogen starvation astaxanthin-producing positive control. The results suggest that all the average chlorophyll dry weight concentration declined among all the EE treatments in both exponential and stationary phase *H. pluvialis* cells during the 12 days cultivation period. Meanwhile, 30 mins EE plus N treatments and 10 mins EE plus N treatments from exponential and stationary phase *H. pluvialis* cells demonstrated an increase in average astaxanthin dry weight concentration but remained unchanged in average chlorophyll dry weight concentration. The average astaxanthin and chlorophyll dry weight concentrations in 60 mins plus N treatments from both exponential and stationary phase *H. pluvialis* cells displayed no reciprocal relationship. Taken together among all the treatments, the chlorophyll level was not suitable to predict the astaxanthin level under the treatments of *H. pluvialis* cells at both exponential and stationary phase.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

What is claimed is:

1. A method of enhancing secondary metabolite accumulation in a microalgal cell culture, said method comprising:
    a) electrically eliciting the microalgal cell culture by exposing said culture to sub-lethal levels of electric current for a period of time during a stationary growth phase of the microalgal cell culture; and
    b) depriving the microalgal cell culture of nitrogen during the stationary growth phase, wherein combining electrical elicitation and nitrogen deprivation increases production of the secondary metabolite.

2. The method of claim 1, wherein the microalgal cell culture comprises *Haematococcus pluvialis* cells.

3. The method of claim 2, wherein the secondary metabolite is astaxanthin.

4. The method of claim 1, wherein electrical elicitation comprises placing electrodes in the microalgal cell culture, wherein the electrodes are operatively coupled to a power source, and the electrodes supply said sub-lethal levels of electric current.

5. The method of claim 1, wherein the sub-lethal levels of electric current ranges from about 30 mA to about 400 mA of direct current or alternating current.

6. The method of claim 1, wherein the period of time for electrical elicitation ranges from about 10 minutes to about 60 minutes.

7. The method of claim 1, further comprising mixing the microalgal cell culture during electrical elicitation to prevent ionic gradients.

8. The method of claim 1, further comprising incubating the microalgal cell culture after electrical elicitation.

9. The method of claim 1, wherein the microalgal cell culture is cultivated for a period of about 10-20 days.

10. The method of claim 1, further comprising electrically eliciting the microalgal cell culture during an exponential growth phase.

11. The method of claim 1, wherein the secondary metabolite is astaxanthin.

* * * * *